United States Patent [19]

Barak

[11] Patent Number: 4,866,094
[45] Date of Patent: Sep. 12, 1989

[54] FUMIGANT METHOD AND COMPOSITIONS COMPRISING 2,2-DIBROMO-3-NITRILOPROPIONAMIDE FOR TREATING CROPS

[75] Inventor: Ayala Barak, Jerusalem, Israel

[73] Assignee: Bromine Compounds Limited, Israel

[21] Appl. No.: 180,389

[22] Filed: Apr. 12, 1988

[30] Foreign Application Priority Data

Apr. 22, 1987 [IL] Israel ................................. 82279

[51] Int. Cl.$^4$ ............................................ A01N 37/34
[52] U.S. Cl. ..................................... 514/528; 514/957
[58] Field of Search ................................ 514/528, 957

[56] References Cited

U.S. PATENT DOCUMENTS 2,419,888  4/1947  Nolan et al. .................... 514/528
4,761,427  8/1988  Segall et al. .................... 514/528

Primary Examiner—Allen J. Robinson
Attorney, Agent, or Firm—Lerner, David, Littenberg, Krumholz & Mentlik

[57] ABSTRACT

A method for treating crops against fungal and bacterial infections by fumigation with 2,2-dibromo-3-nitrilopropionamide (DBNPA) is described. The method is particularly useful in potato crops. Fumigant compositions comprising DBNPA which are useful in the invention are also disclosed.

9 Claims, No Drawings

FUMIGANT METHOD AND COMPOSITIONS COMPRISING 2,2-DIBROMO-3-NITRILOPROPIONAMIDE FOR TREATING CROPS

The present invention relates to a method for treating crops against fungal and bacterial infections by fumigation, and to fumigant compositions therefor. Particularly, the invention relates to the use of 2,2-dibromo-3-nitrilopropionamide (DBNPA) as a fumigant for biocidal applications.

One of the crops most suffering from both fungal and bacterial attack is potatoes, to which particular attention has been given in the art, and which will be discussed in detail in the following description. Potato diseases are caused by fungi and bacteria. These microorganisms attack both grown and seed potatoes, and throughout this specification, whenever reference is made to potatoes, it is understood that both grown and seed potatoes are meant, as applicable. Numerous factors influence the amount of disease exression in a potato crop, such as environmental conditions, interaction between different pathogens, cultivar resistance or succeptibility, plant nutrition, seed handling, etc. Many efforts have been directed to the control of potato diseases, because of the economic value of this crop.

A large number of biocidals is employed to treat potato crops, notably the organo-mercury compounds. These, as well as other commonly employed biocides, present severe drawbacks, since they are toxic and phytotoxic. Among the best known fungicidal compounds, Caspan (3-methoxyethylmercury chloride) and Captan (tetrahydro-2-[(trichloromethyl)thio]-4-cyclohexene-1,2-dicarboximide) are commonly employed in the art.

Among the most common microorganisms which attack potatoes, there are found *Erwinia carotovora, Streptomyces scabies, Fusarium oxysporum, Verticillium dahliae* and *Rhizoctonia solani*. Among these, Erwinia car.—which is a major responsible for potato diseases and *Streptomyces scabies* are bacteria, and *Fusarium oxysporum, Verticillium dahliae* and *Rhiaoctonia solani* are fungi.

Few of the chemicals used on potatoes have appreciable volatility and fungicidal activity is often confined to sites of initial deposition, so that total cover of the tuber is essential. This is of course a severe drawback which reflects on the cost nd quality of potato treatments. Several methods of application are known in the art. Total immersion of tubers is often employed which, however, is hazardous because of the risk of soft rot in the treated tubers and blackleg in the crop. Dusting by shaking or rolling in fungicide powder is often employed. This method, however, is relatively complex and the amount of fungicide reaching the tuber is dependent on the inert carrier. Spraying of mists is also employed. This method is technically complex, requires rotation of tubers, the spray liquid is often a suspension and relatively large amounts of spray are required. Among the chemicals normally employed for the control of fungal and bacterial diseases the organo-mercury compounds are often employed to treat potatoes.

Fumigation is a method which overcomes many of these drawbacks, besides being simple and economic. The problems connected with fumigations are the low volatility of the commonly employed chemicals and that they are harmful in vapour form. The art has therefore long felt a want of a fumigant formulation which is relatively non-hazardous and which can be employed in crop fumigation.

In a copending patent application by the same applicant there is described the sporicidal and fungicidal activity of DBNPA. The applicant has discovered that this known bactericidal possesses unexpected sporicidal and fungicidal properties.

It has now been most surprisingly found, and this is an object of the present invention, that DBNPA, notwithstanding its exceedingly low volatility, can also be conveniently employed as a fumigant, and that fumigation therewith provides an excellent biocidal effect, both against fungi and bacteria.

It has further been found, and this is a further object of the invention, that fumigation with DBNPA is particularly effective against fungi and bacteria which are responsible for potato diseases.

By fumigation it is meant the delivery of biocidally effective amounts of DBNPA to the locus to be treated against microorganisms from a reservoir containing DBNPA, either alone or in admixture with solvents and/or other biocidal or biocidally inert compounds, through a gas as the transfer medium, without any direct contact between the material contained in the reservoir and the locus to be treated.

The fumigant biocidal composition according to the invention is characterized in that it comprises as an active ingredient 2,2-dibromo-3-nitrilopropionamide, alone or in admixture with an organic solvent or an organic solvent and/or water.

The organic solvent, in order to be suitably employed in the compositions of the invention, must of course be usable with the crops involved. For instance, if edible crops are treated, the solvent must be such that it does not remain for long periods on the crop and is not toxyc or phytotoxic. Preferably, the organic solvent is a glycol selected from mono-, di- or poly-propylene glycol, more preferably, dipropylene glycol.

A preferred fumigant composition of the invention comprises:
 0 to 100 wt% of 2,2-dibromo-nitrilopropionamide, preferably about 20 wt%;
 0 to 80 wt% organic solvent, preferably about 60%; and
 0 to 80 wt% water, preferably about 20 wt%.

The method of treating crops infected with microorganisms according to the invention is characterized in that the crop to be treated is fumigated with a fumigant biocidal composition according to the invention.

A crop particularly suitable for being treated by the method of the invention is potatoes or seed potatoes.

The microorganism may be any microorganism which attacks crops, and particularly the method can be conveniently carried out to destroy *Erwinia carotovora* or *Streptomyces scabies* or *Fusarium oxysporum* or *Verticillium dahliae* or *Rhizoctonia solani*, or two or more of the said microorganisms present on a given crop at the same time.

The above and other characteristics and advantages of the invention will be better understood through the following illustrative and non limitative examples. In all cases the high temperature (>37° C.) experiments were carried out in a fumigation cell having a total volume of 15 lit., containing a controlled heating unit located at the centre of an insulating block. Two aluminium plates (3 ml volume each) were placed on the heating unit. The agar plates were placed above the heating unit at room temperature. The biocidal formulation was heated to the chosen temperature, and the plates were then placed in the closed cell for the required period. After removing the plates, they were incubated at 27° C. for 24 hours, and viable counts were compared to those of parallel control experiments. Experiments at lower temperatures were carried out in a fumigation vessel maintained throughout at the designated temperature, as will be further described in the examples.

EXAMPLE 1

Fumigation experiments were carried out in the fumigation cell, to test the efficacy of two different formulations of DBNPA against *Erwinia carotovora* ATCC 15713, at different temperatures. The results of these tests are shown in Table I. The fumigant compositions employed were a solid form, comprising DBNPA alone, and a liquid formulation containing dipropylene glycol (DPG) (20:20:60 wt% DBNPA:WATER:DPG), marked (s) and (l) in Table I respectively. Liquid formulations containing a glycol also contained in each case 0.1% buthylated hydroxytoluene (BHT) as antioxidant. As can be appreciated from Table I, the efficacy of the liquid formulation is appreciably higher than that of the solid form, and a sensible effect of the fumigation cell temperature can be seen. The total weight of the active material is not important, as long as some active material remains at the end of the experiment, and the important factor is its evaporation rate. The actual weight of the active material in liquid formulations can be calculated on the basis of the amounts employed in each case.

EXAMPLE 2

Example 1 was repeated at low temperatures (4°, 27° and 37° C.), and the results of these tests are shown in Table II. The Erwinia spores were placed in shake flasks containing 50 ml cell suspension, and vials containing the biocide formulation were hanged above the water level, within the fumigation vessel. As it is seen from the comparison of Tables I and II, longer contact times are required for lower fumigation temperatures.

EXAMPLE 3

The efficacy of DBNPA against three fungi and one bacteria was tested in the fumigation cell. The fungi employed were *Fusarium oxy.*, *Verticillium dahliae* and *Rhiaoctonia sol.* and the bacteria was *Streptomyces scabies*. The results are reported in Table III.

All experiments were carried out at 70° C. and with different initial inoculum. The fumigation cell was charged with a 20:20:60 DBNPA:WATER:DPG formulation. In all cases no survivors were found for al fungi tested, while the times were too short for total killing of *Streptomyces scabies*.

EXAMPLE 4

A singlesample of a 20:20:60 formulation of DBNPA in DPG and water was used for a long-term fumigation experiment, in order to test the long term activity of such a formulation. The fumigation experiment was carried out at 70° C., with contact times of 1 hour for each plate, the plates being inoculated with *Erwinia carotovora*. Two identical samples of the formulation were employed in the experiment. The results of this test are shown in Table IV. The cell was operated for an overall 61 hours nd retained its activity against Erwinia during 55 hours. Water was seen to evaporate quickly and after the first 5 hours a make-up of water was added to the formulation. The weight loss per hour of an hydrated sample was about 20%/hour, while the average weight loss of a dehydrated sample was 1.5%, which accounts for an evaporation rate of DBNPA of less than 0.4%/hour (about 30 mg/hr), if the evaporation rate is taken as constant.

EXAMPLE 5

A number of experiments were carried out, in order to test the relative efficacy of different mixtures of solid DBNPA and water. The results of these tests are shown in Table V. The weight losses are reported for each of the two identical samples of aqueous formulation employed together in the experiment.

The fumigation temperature was kept at 70° C. throughout the experiments. The best results were obtained with compositions containing 20 wt% DBNPA in water. This formulation provided results sensibly better than any solid/aqueous formulation tested, and similar to the results of the formulation containing DPG. It should also be noted that the evaporation rates in two identicall cells differ within unpredictable limits. This is believed to be due to the non-homogeinity of a formulation of DBNPA in water alone.

EXAMPLE 6

Fumigation experiments were carried out with several ingredients of the DBNPA formulations and with DBNPA analogues, in order to measure their fumigation biocidal activity and compare it with the fumigation efficacy of the compositions of the invention. All fumigation experiments were carried out at 70° C., and two microorganisms were tested: *Erwinia carotovora* subsp. carotovora (ATCC 15713), and spores of *Fusarium oxysporum* (isolated from contaminated crops).

The results are summarized in Table VI. The fumigant compositions tested, as identified in the table, were as follows:

DPG—pure dipropylene glycol;
EG—pure ethylene glycol;
$Br_2$—a formulation of 7% $Br_2$ and 23% $H_2O$ in 70% DPG;
Monobromo—a formulation of 25% monobromocyanoacetamide (MBNPA, prepared by mixing equimolar quantities of DBNPA and cyanoacetamide), 19% $H_2O$ and 56% DPG;
DBNPA/EG—a formulation containing 20% DBNPA, and 20% $H_2O_2$ in 60% EG;
DBNPA/DPG—a formulation containing 20% DBNPA, 20% $H_2O$ and 60% DPG;
The percentages given above are by weight.

The two solvents DPG and EG did not show any biocidal activity under the test conditions. The $Br_2$ formulation exhibited some biocidal properties, giving a partial control with long contact times (1 hour). The DBNPA/EG formulation controlled *Erwinia car.* to some extent, when a contact time of 1 hour was examined, and controlled low inoculum of *Fusarium oxy.* ($8 \times 10^5$ spores/plate) with a contact time of half an hour, and the high inoculum ($8 \times 10^7$ spores/plate) using a contact time of 1 hour. DBNPA/DPG was effective against both Erwinia sp. and *Fusarium oxy.*, after 15 minutes of fumigation.

The above description and examples have been given for the purpose of illustration and are not intended to be limitative. Different fumigation cells and methods can be employed, for instance, and different microorganisms destroyed, or different solid or liquid formulations used, without exceeding the scope of the invention.

TABLE 1

Efficacy of DBNPA Formulations against Erwinia in Fumigation

| Initial count | Temp. (°C.) | Contact time (h) | Biocide content | No. of survivors per plate |
|---|---|---|---|---|
| $5 \cdot 10^7$ | 50 | 4 | 23.20 gr (s) | $5 \cdot 10^7$ |
| $5 \cdot 10^5$ | 50 | 4 | 23.20 gr (s) | $5 \cdot 10^5$ |
| $5 \cdot 10^3$ | 50 | 4 | 23.20 gr (s) | $5 \cdot 10^3$ |
| $6 \cdot 10^7$ | 100 | 4 | 23.20 gr (s) | no survivors |
| $6 \cdot 10^5$ | 100 | 4 | 23.20 gr (s) | no survivors |
| $6 \cdot 10^3$ | 100 | 4 | 23.20 gr (s) | no survivors |
| $1 \cdot 10^7$ | 70 | 2 | 23.20 gr (s) | $\sim 10^7$ |
| $1 \cdot 10^5$ | 70 | 2 | 23.20 gr (s) | $\sim 10^3$ |
| $1 \cdot 10^3$ | 70 | 2 | 23.20 gr (s) | 10 |
| $8 \cdot 10^6$ | 70 | 4 | 6 ml (l) | no survivors |
| $8 \cdot 10^4$ | 70 | 4 | 6 ml (l) | no survivors |
| $8 \cdot 10^2$ | 70 | 4 | 6 ml (l) | no survivors |
| $4 \cdot 10^7$ | 70 | 2 | 6 ml (l) | no survivors |
| $4 \cdot 10^5$ | 70 | 2 | 6 ml (l) | no survivors |
| $4 \cdot 10^3$ | 70 | 2 | 6 ml (l) | no survivors |
| $3 \cdot 10^8$ | 70 | 1 | 6 ml (l) | no survivors |
| $3 \cdot 10^6$ | 70 | 1 | 6 ml (l) | no survivors |
| $3 \cdot 10^4$ | 70 | 1 | 6 ml (l) | no survivors |
| $2 \cdot 10^8$ | 70 | 0.5 | 6 ml (l) | $\sim 10^8$ |
| $2 \cdot 10^6$ | 70 | 0.5 | 6 ml (l) | $\sim 10^5$ |
| $2 \cdot 10^4$ | 70 | 0.5 | 6 ml (l) | $\sim 10^3$ |
| $4 \cdot 10^7$ | 90 | 1 | 23 gr (s) | $\sim 10^6$ |
| $4 \cdot 10^5$ | 90 | 1 | 23 gr (s) | $\sim 10^4$ |
| $4 \cdot 10^3$ | 90 | 1 | 23 gr (s) | $\sim 10^2$ |
| $4 \cdot 10^7$ | 90 | 1 | 6 ml (l) | no survivors |
| $4 \cdot 10^5$ | 90 | 1 | 6 ml (l) | no survivors |
| $4 \cdot 10^3$ | 90 | 1 | 6 ml (l) | no survivors |
| $4 \cdot 10^7$ | 90 | 0.5 | 6 ml (l) | no survivors |
| $4 \cdot 10^5$ | 90 | 0.5 | 6 ml (l) | no survivors |
| $4 \cdot 10^3$ | 90 | 0.5 | 6 ml (l) | no survivors |

TABLE II

Fumigation of Erwinia at Room Temperature

| Initial count | Temp (°C.) | Contact time (hrs) | Biocide | No. of Survivors per plate |
|---|---|---|---|---|
| $2 \times 10^8$/c'c | 37 | 24 | 1.5 gr (s) | $3 \times 10^8$ |
| $2 \times 10^7$/c'c | 37 | 24 | 1.5 gr (s) | $3 \times 10^8$ |
| $2 \times 10^8$/c'c | 37 | 24 | 3.0 gr (s) | $1 \times 10^8$ |
| $2 \times 10^7$/c'c | 37 | 24 | 3.0 gr (s) | $5 \times 10^7$ |
| $5 \times 10^7$/c'c | 37 | 24 | 3.0 ml (l) | no survivors |
| $5 \times 10^7$/c'c | 37 | 24 | 4.5 ml (l) | no survivors |
| $5 \times 10^7$/c'c | 37 | 24 | 6.0 ml (l) | no survivors |
| $9 \times 10^6$/c'c | 27 | 24 | 3.0 ml (l) | no survivors |
| $9 \times 10^6$/c'c | 27 | 24 | 4.5 ml (l) | no survivors |
| $9 \times 10^6$/c'c | 27 | 24 | 6.0 ml (l) | no survivors |
| $4 \times 10^7$/c'c | 4 | 96 | 3.0 ml (l) | no survivors |
| $4 \times 10^7$/c'c | 4 | 96 | 4.5 ml (l) | no survivors |
| $4 \times 10^7$/c'c | 4 | 96 | 6.0 ml (l) | no survivors |

TABLE III

Efficacy of a DBNPA Formulation Against Various MO's

| Type of MO | Temp (°C.) | Contact time (h) | Inoculum cfu/plate | Survivors cfu/plate |
|---|---|---|---|---|
| Fusarium oxy. | 70 | 1 | $3 \times 10^5$ | — |
| | 70 | 0.5 | $3 \times 10^5$ | — |
| | 70 | 0.5 | $1 \times 10^7$ | — |
| | 70 | 1 | $1 \times 10^7$ | — |
| Streptomyces scabies | 70 | 1 | $2 \times 10^5$ | $2 \times 10^3$ |
| | 70 | 1 | $2 \times 10^4$ | $2 \times 10^2$ |
| | 70 | 1 | $2 \times 10^3$ | $2 \times 10$ |
| | 70 | 0.5 | $2 \times 10^5$ | $2 \times 10^5$ |
| | 70 | 0.5 | $2 \times 10^4$ | $8 \times 10^3$ |
| | 70 | 0.5 | $2 \times 10^3$ | $2 \times 10^3$ |
| Verticillium dahliae | 70 | 0.5 | $5 \times 10^5$ | — |
| | 70 | 0.5 | $5 \times 10^3$ | — |
| | 70 | 0.5 | $5 \times 10$ | — |
| | 70 | 1 | $5 \times 10^5$ | — |
| | 70 | 1 | $5 \times 10^3$ | — |
| | 70 | 1 | $5 \times 10$ | — |
| | 70 | 0.25 | $6 \times 10^5$ | — |
| | 70 | 0.5 | $6 \times 10^5$ | — |
| Rhizoctonia sol. | 70 | 1 | mycellia 0.5 cm covered plate | — |
| | 70 | 2 | | — |

TABLE IV

Fumigation of Erwinia Carotovora with a Single Sample of Fumigant

| Overall fumigation time (hrs) | Initial weight (gr) A | Initial weight (gr) B | Average weight loss per hour (%) | Initial count cfu/plate | Survivors |
|---|---|---|---|---|---|
| 1 | 3.44 | 3.44 | 19 | $1 \times 10^8$ | — |
| 2 | 2.83 | 2.78 | 1.2 | $1 \times 10^8$ | — |
| 3 | 2.76 | 2.77 | 0 | $1 \times 10^8$ | — |
| 4 | 2.79 | 2.73 | 1.2 | $1 \times 10^8$ | — |
| 5 | 2.73 | 2.72 | 0.5 | $1 \times 10^8$ | — |
| 6* | 3.49 | 3.52 | 19 | $1 \times 10^8$ | — |
| 7–12 | 2.33 | 1.25 | 1.5 | $1 \times 10^8$ | — |
| 13–18 | 2.14 | 1.13 | 1.9 | $1 \times 10^8$ | — |
| 19–24 | 2.04 | 1.03 | 2.3 | $1 \times 10^8$ | — |
| 25–28 | 1.81 | 0.89 | 1.9 | $1 \times 10^7$ | — |
| 29–32 | 1.74 | 0.82 | 1.8 | $1 \times 10^7$ | — |
| 33–35 | 1.70 | 0.78 | 2.3 | $9 \times 10^7$ | — |
| 36–42 | 1.64 | 0.73 | 1.8 | $5 \times 10^7$ | — |
| 43–49 | 1.50 | 0.65 | 2.6 | $3 \times 10^7$ | — |
| 50–55 | 1.35 | 0.53 | 1.33 | $3 \times 10^7$ | — |
| 56–61 | 1.28 | 0.50 | 1 | $3 \times 10^7$ | + |

*20% water was added to the residue prior to fumigation

TABLE V

Fumigation of Erwinia Using Solid DBNPA in Water Formulation

| Mixture H2O (%) | solid DBNPG (%) | Contact time (hours) | Inoculum (cfu/plate) | Survivors (cfu/plate) | Weight loss (%) |
|---|---|---|---|---|---|
| 20 | 80 | 0.5 | $5 \times 10^8$ | $5 \times 10^8$ | — |
| 50 | 50 | 0.5 | $5 \times 10^8$ | $5 \times 10^8$ | 41,50 |
| 50 | 50 | 1 | $4 \times 10^8$ | 50% kill | 26,18 |
| 50 | 50 | 1 | $4 \times 10^6$ | 80% kill | 26,18 |
| 50 | 50 | 1 | $4 \times 10^8$ | 50% kill | 14,31 |
| 50 | 50 | 1 | $4 \times 10^6$ | no survivors | 26,18 |
| 80 | 20 | 1.5 | $4 \times 10^8$ | no survivors | 51,58 |
| 80 | 20 | 0.5 | $4 \times 10^8$ | no survivors | 4,17 |
| 80 | 20 | 1 | $4 \times 10^8$ | no survivors | 57,80 |
| 20 | 80 | 1 | $2 \times 10^9$ | $2 \times 10^8$ | 22,19 |
| 20 | 80 | 1 | $2 \times 10^7$ | no survivors | |
| 20 | 80 | 0.5 | $2 \times 10^9$ | $2 \times 10^9$ | 17,20 |
| 20 | 80 | 0.5 | $2 \times 10^7$ | $2 \times 10^6$ | |
| 50 | 50 | 1 | $2 \times 10^9$ | $2 \times 10^7$ | 49,25 |
| 50 | 50 | 0.5 | $2 \times 10^9$ | $2 \times 10^8$ | 37,50 |
| 50 | 50 | 0.5 | $2 \times 10^7$ | $2 \times 10^6$ | |

TABLE V-continued

Fumigation of Erwinia Using Solid DBNPA in Water Formulation

| Mixture | | Contact | | | |
|---|---|---|---|---|---|
| $H_2O$ (%) | solid DBNPG (%) | time (hours) | Inoculum (cfu/plate) | Survivors (cfu/plate) | Weight loss (%) |
| 80 | 20 | 0.5 | $2 \times 10^9$ | no survivors | 54,31 |
| 80 | 20 | 0.5 | $2 \times 10^7$ | no survivors | 54,31 |
| 80 | 20 | 1 | $2 \times 10^9$ | no survivors | 50,61 |

TABLE VI

Comparison of the Fumigation Efficacy of Various Ingredients and analogues of DBNPA formulations, at 70°C.

| Active Ingredient | Type of MO | Contact time (hours) | Inoculum spores or cfu per plate | Weight loss % | Number of survivors cfu/plate |
|---|---|---|---|---|---|
| DPG | Erwin. | 0.5 | $1 \times 10^4$ | Not detectable | Grows like control |
| DPG | Erwin. | 1 | $1 \times 10^4$ | Not detectable | Grows like control |
| DPG | Fus.oxy. | 0.5 | $2 \times 10^6$ | Not detectable | Grows like control |
| DPG | Fus.oxy. | 1 | $2 \times 10^6$ | Not detectable | Grows like control |
| EG | Erwin. | 0.5 | $1 \times 10^4$ | Not detectable | Grows like control |
| EG | Erwin. | 1 | $1 \times 10^4$ | Not detectable | Grows like control |
| EG | Fus.oxy. | 0.5 | $2 \times 10^6$ | Not detectable | Grows like control |
| EG | Fus.oxy. | 1 | $2 \times 10^6$ | Not detectable | Grows like control |
| $Br_2$ | Erwin. | 0.25 | $1 \times 10^4$ | 9% | Growth |
| $Br_2$ | Erwin. | 0.5 | $1 \times 10^4$ | Not measured | Growth |
| $Br_2$ | Erwin. | 1 | $1 \times 10^4$ | Not measured | Growth |
| $Br_2$ | Fus.oxy. | 0.25 | $2 \times 10^6$ | 9% | Grows like control |
| $Br_2$ | Fus.oxy. | 0.25 | $2 \times 10^4$ | 9% | Grows less than control |
| $Br_2$ | Fus.oxy. | 0.5 | $2 \times 10^6$ | Not measured | Some growth |
| $Br_2$ | Fus.oxy. | 0.5 | $2 \times 10^4$ | Not measured | Some growth |
| $Br_2$ | Fus.oxy. | 1 | $1 \times 10^6$ | Not measured | Some growth |
| $Br_2$ | Fus.oxy. | 1 | $2 \times 10^4$ | Not measured | Some growth |
| Monobromo | Erwin. | 0.25 | $1 \times 10^4$ | 7% | Some growth |
| Monobromo | Erwin. | 0.5 | $1 \times 10^4$ | 10% | Some growth |
| Monobromo | Erwin. | 1 | $1 \times 10^4$ | 11% | 45 |
| Monobromo | Fus.oxy. | 0.25 | $2 \times 10^6$ | 7% | Some growth |
| Monobromo | Fus.oxy. | 0.5 | $2 \times 10^6$ | 10% | Some growth |
| Monobromo | Fus.oxy. | 1 | $2 \times 10^6$ | 11% | No growth |
| DBNPA/EG | Erwin. | 0.25 | $1 \times 10^8$ | 4% | Grows like control |
| DBNPA/EG | Erwin. | 0.5 | $1 \times 10^8$ | 11% | 10 |
| DBNPA/EG | Erwin. | 1 | $1 \times 10^8$ | 3% | Some growth |
| DBNPA/EG | Fus.oxy. | 0.25 | $8 \times 10^7$ | 4% | Growth |
| DBNPA/EG | Fus.oxy. | 0.25 | $8 \times 10^5$ | 4% | 10 |
| DBNPA/EG | Fus.oxy. | 0.5 | $8 \times 10^7$ | 11% | 1 |
| DBNPA/EG | Fus.oxy. | 0.5 | $8 \times 10^5$ | 11% | 11 |
| DBNPA/EG | Fus.oxy. | 1 | $8 \times 10^7$ | 3% | No growth |
| DBNPA/EG | Fus.oxy. | 1 | $8 \times 10^5$ | 3% | No growth |
| DBNPA/DPG | Erwin. | 0.25 | $1 \times 10^8$ | 2% | No growth |
| DBNPA/DPG | Erwin. | 0.5 | $1 \times 10^8$ | 16% | No growth |
| DBNPA/DPG | Fus.oxy. | 0.25 | $8 \times 10^7$ | 2% | No growth |
| DBNPA/DPG | Fus.oxy. | 0.5 | $8 \times 10^7$ | 16% | No growth |

What we claim is:

1. A method for treating crops against fungal and bacterial infections comprising fumigating said infected crops with an effective fungicidal and bactericidal amount of 2,2-dibromo-3-nitrilopropionamide through a gas as the transfer medium, said biocidal composition being generated from a reservoir whereby said composition contained in said reservoir comprises a solid or liquid composition which does not directly contact said infected crops.

2. The method according to claim 1 wherein said composition contained in said reservoir includes a non-toxic organic solvent, water or mixture thereof.

3. The method according to claim 2 wherein said composition contained in said reservoir includes up to about 80% by weight of said organic solvent.

4. The method according to claim 2 wherein said composition contained in said reservoir includes up to about 80% by weight of said water.

5. The method according to claim 2 wherein said organic solvent comprises a glycol selected from the group consisting of mono, di-, and polypropylene glycol.

6. The method according to claim 5 wherein the glycol comprises dipropylene glycol.

7. The method according to claim 5, wherein the composition comprises:
 (1) about 20% by weight of 2,2 dibromo-3-nitrilopropionamide;
 (2) about 60% by weight of an organic solvent; and
 (3) about 20% by weight of water.

8. The method according to claim 1 wherein said infected crops comprise potatoes or seed potatoes.

9. The method according to claim 8, wherein said fungal and bacterial infections are produced by microorganisms selected from the group consisting of ervinia caratovora, streptomyces scabies, fusarium oxysporum, verticullum dahliae, rhizoctonia solani and mixtures thereof.

* * * * *